(12) United States Patent
Laut

(10) Patent No.: US 8,596,495 B2
(45) Date of Patent: Dec. 3, 2013

(54) METER FOR A DEVICE FOR DISTRIBUTING A FLUID OR POWDER PRODUCT

(75) Inventor: Antoine Laut, Etrepagny (FR)

(73) Assignee: Aptar France SAS, Le Neubourg (FR)

( * ) Notice: Subject to any disclaimer, the term of this patent is extended or adjusted under 35 U.S.C. 154(b) by 0 days.

(21) Appl. No.: 13/142,799

(22) PCT Filed: Dec. 28, 2009

(86) PCT No.: PCT/FR2009/052705
§ 371 (c)(1),
(2), (4) Date: Jun. 29, 2011

(87) PCT Pub. No.: WO2010/076528
PCT Pub. Date: Jul. 8, 2010

(65) Prior Publication Data
US 2011/0266306 A1   Nov. 3, 2011

(30) Foreign Application Priority Data

Dec. 30, 2008  (FR) ..................... 08 59142

(51) Int. Cl.
*B67D 7/22* (2010.01)
(52) U.S. Cl.
USPC ....................... 222/36; 128/205.23
(58) Field of Classification Search
USPC ........ 222/47–49, 36–38; 128/205.23, 203.15, 128/200.11–200.14; 215/230; 116/309–318
See application file for complete search history.

(56) References Cited

U.S. PATENT DOCUMENTS

| | | | | |
|---|---|---|---|---|
| 7,322,352 B2* | 1/2008 | Minshull et al. | .......... | 128/203.15 |
| 7,387,122 B2* | 6/2008 | Nishibayashi et al. | .. | 128/203.15 |
| 7,882,982 B2* | 2/2011 | Stradella et al. | ................ | 222/38 |
| 8,113,199 B2* | 2/2012 | Augustyn et al. | ........ | 128/205.23 |
| 8,186,343 B2* | 5/2012 | Stradella et al. | .......... | 128/200.14 |
| 8,245,906 B2* | 8/2012 | Crosby et al. | ................ | 235/91 R |
| 2010/0212664 A1* | 8/2010 | Bishop | ..................... | 128/200.23 |

FOREIGN PATENT DOCUMENTS

| WO | 2007/077450 A2 | 7/2007 |
|---|---|---|
| WO | 2007/104964 A1 | 9/2007 |

OTHER PUBLICATIONS

International Search Report PCT/FR2009/052705, Mar. 9, 2010.

* cited by examiner

*Primary Examiner* — Lien Ngo
(74) *Attorney, Agent, or Firm* — Sughrue Mion, PLLC

(57) ABSTRACT

A dose counter (100) for counting the number of doses of fluid or powder that have been dispensed or that remain to be dispensed from a fluid dispenser device (200), said counter including a first rotary counter element forming a units wheel, and a second rotary counter element forming a tens wheel, said first and second counter elements co-operating with each other to define and to display, in a viewing window (151), said number of doses, said first counter element co-operating with an actuator member that is adapted to cause said first counter element to turn each time said actuator member is actuated, said counter including a base body that incorporates a pivot pin for said first and second counter elements and an opening, said counter possibly being pre-assembled in said base body so as to form a pre-assembled counter unit.

20 Claims, 8 Drawing Sheets

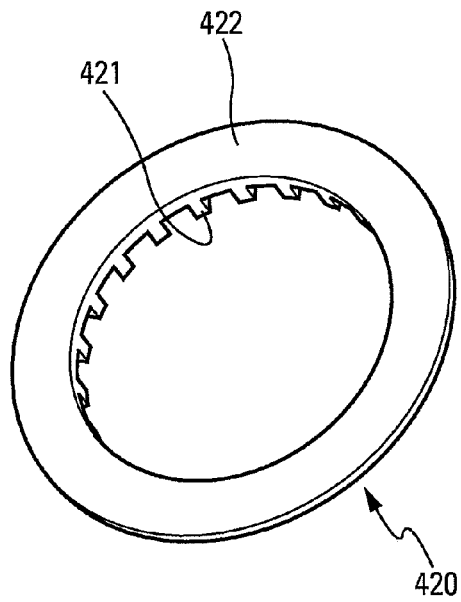
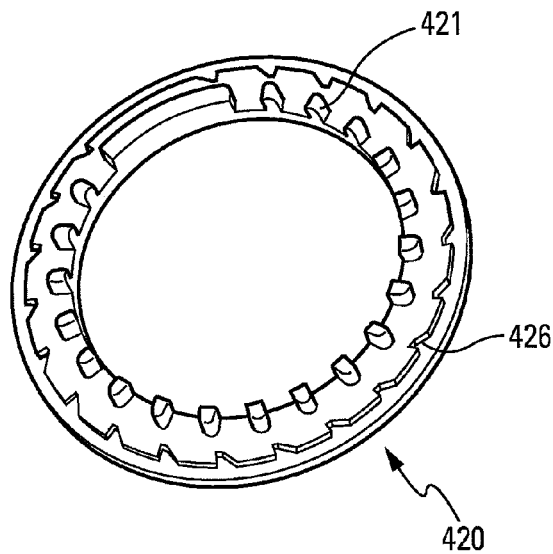
Fig. 16a          Fig. 16b
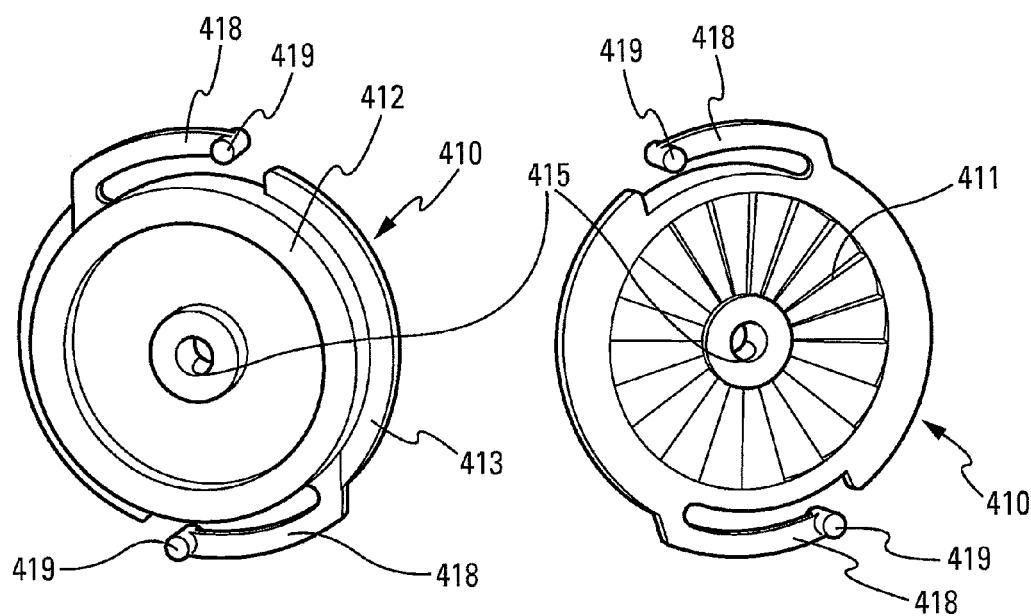
Fig. 17a          Fig. 17b

METER FOR A DEVICE FOR DISTRIBUTING A FLUID OR POWDER PRODUCT

CROSS REFERENCE TO RELATED APPLICATIONS

This application is a National Stage of International Application No. PCT/FR2009/052705 filed Dec. 28, 2009, claiming priority based on French Patent Application No. 0859142 filed Dec. 30, 2008, the contents of all of which are incorporated herein by reference in their entirety.

The present invention relates to a counter, and more particularly to a dose counter, for indicating to the user the number of doses that have been dispensed or that remain to be dispensed from a fluid or powder dispenser device.

The use of counters or of indicators is well known in the field of fluid dispensers, in particular in the field of pharmaceuticals. In particular, such counters or indicators are used with dispenser devices of the metered dose inhaler (MDI) type, in which a reservoir containing fluid and a propellant gas is movably mounted in a body, movement of said reservoir actuating a metering valve mounted on said reservoir, so as to dispense a dose of fluid. A first family of counters envisages fastening the counter on the bottom of the reservoir, projecting out from the body, and on which the user presses in order to dispense a dose. However, that type of counter presents the drawback of interfering with the actuation of the dispenser device, with it being necessary for the user to press on the counter in order to actuate the device. In the event of poorly controlled or partial actuation, problems of over- and/or under-counting and/or of incomplete or faulty dispensing may thus occur. A second family of counters comprises counters that are disposed inside the body, being fastened either to the body or to the movable reservoir in said body. In particular, that type of counter presents the drawback of a complex mounting, and requires substantial modifications to the various component parts of the dispenser device. The assembly problem occurs in particular when assembly is performed by the manufacturer of the pharmaceutical, as opposed to by the manufacturer of the dispenser device, with that requiring the manufacturer of the pharmaceutical to install complex assembly machines in its own factory. A third family of counters envisages arranging the counter on an outside face of the body, a projection of said counter passing through an opening in the body, so as to co-operate with the reservoir or a portion that is secured to said reservoir. That type of counter also generally requires substantial modification to the body in order to receive the counter. In addition, the presence of a counter on the outside main face of the body substantially modifies the external appearance of the device, in particular because of the thickness of said counter, and that may also have a negative effect on the handling of the device. In addition, the counters used on dispenser devices for dispensing fluids, in particular pharmaceuticals, need to comply with several constraints. Thus, in order to avoid any risk of under-counting, it is generally required that the counter is actuated at the very beginning of the actuation stroke of the valve or the pump, so as to avoid partial actuation, causing a partial or complete dose to be dispensed without any dose being counted by the counter. In this situation, a problem that occurs is that the actuation stroke is generally very short, and that the manufacturing tolerances of the device tend to reduce even further the distance available to perform the actuation in effective manner. The use of a complex mechanism is generally required in order to provide counting that is functional and safe. In general, assembling counters, in particular counters including a plurality of rotary elements that are interleaved in one another, is found to be complex and thus not only costly, but also a source of malfunctions. Documents WO 2007/077450 and WO 2007/104964 describe prior-art counters.

An object of the present invention is to provide a counter, more particularly a dose counter, for a fluid or powder dispenser device, that does not reproduce the above-mentioned drawbacks.

In particular, an object of the present invention is to provide such a counter that presents minimum thickness.

Another object of the present invention is to provide such a counter that can be pre-assembled prior to being delivered to the manufacturer of the pharmaceutical, said manufacturer thus needing only to perform a single step of mounting the counter on the body of the dispenser device, without any complex assembly of the component parts of said counter.

Another object of the present invention is to provide such a counter that guarantees actuation of the counter independently of the length of the actuation stroke of the pump or of the valve used in the device.

Another object of the present invention is to provide such a counter that is simpler and thus less costly to manufacture and to assemble, and that is more reliable in operation.

The present invention thus provides a dose counter for counting the number of doses of fluid or powder that have been dispensed or that remain to be dispensed from a fluid dispenser device, said counter including a first rotary counter element forming a units wheel, and a second rotary counter element forming a tens wheel, said first and second counter elements co-operating with each other to define and to display, in a viewing window, said number of doses, said first counter element co-operating with an actuator member that is adapted to cause said first counter element to turn each time said actuator member is actuated, said counter including a base body that incorporates a pivot pin for said first and second counter elements and an opening, said counter possibly being pre-assembled in said base body so as to form a pre-assembled counter unit.

Advantageously, said counter unit includes fastener means for fastening to a body of a fluid dispenser device.

Advantageously, said base body is associated with a lid that is adapted to be fastened on said base body, after the counter has been assembled in the base body.

In a first advantageous embodiment of the invention, the pre-assembled counter unit, comprising the base body, the actuator member, the intermediate element, the first and second counter elements, and the lid, presents thickness that is less than or equal to 7 millimeters (mm), advantageously less than 6 mm, in particular less than 5 mm.

In a second advantageous embodiment of the invention, the pre-assembled counter unit, comprising the base body, the actuator member, and the first and second counter elements, presents thickness that is less than or equal to 7 mm, advantageously less than 6 mm, in particular less than 5 mm.

The present invention also provides a fluid or powder dispenser device comprising a reservoir, a dispenser member, such as a metering valve, that is mounted on said reservoir, and a body incorporating a dispenser orifice, said reservoir being movable in said body so as to dispense the fluid or powder, said dispenser device including a counter as described above.

Advantageously, said counter is fastened to the body laterally, said device being actuated by the user pressing axially on the reservoir, and said counter being actuated by said axial movement of said reservoir that co-operates with said actuator element of the actuator member.

These characteristics and advantages and others of the present invention appear more clearly from the following detailed description, given by way of non-limiting example, and with reference to the accompanying drawings, in which:

FIGS. 16a and 16b are diagrammatic front and rear views respectively of the second rotary counter element, in an advantageous variant embodiment; and FIGS. 17a and 17b are diagrammatic front and rear views respectively of the first rotary counter element, in an advantageous variant embodiment.

Figure 1:
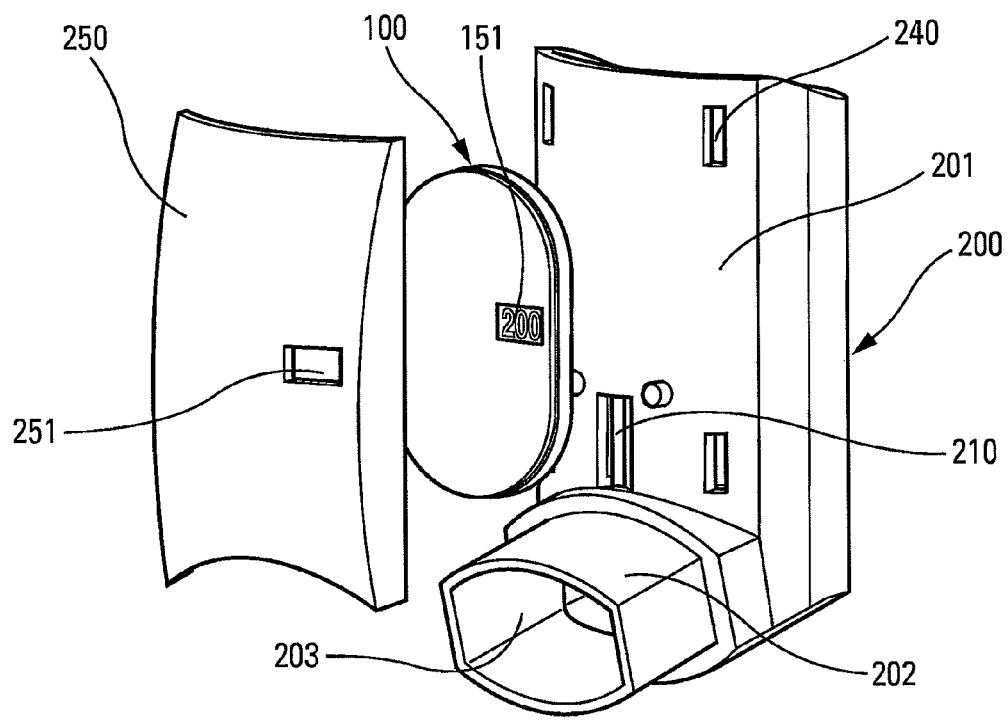
FIG. 1 is an exploded perspective view of a dispenser device including, on its front main face, a counter in a particular embodiment of the present invention.
Figures 2A, 2B:
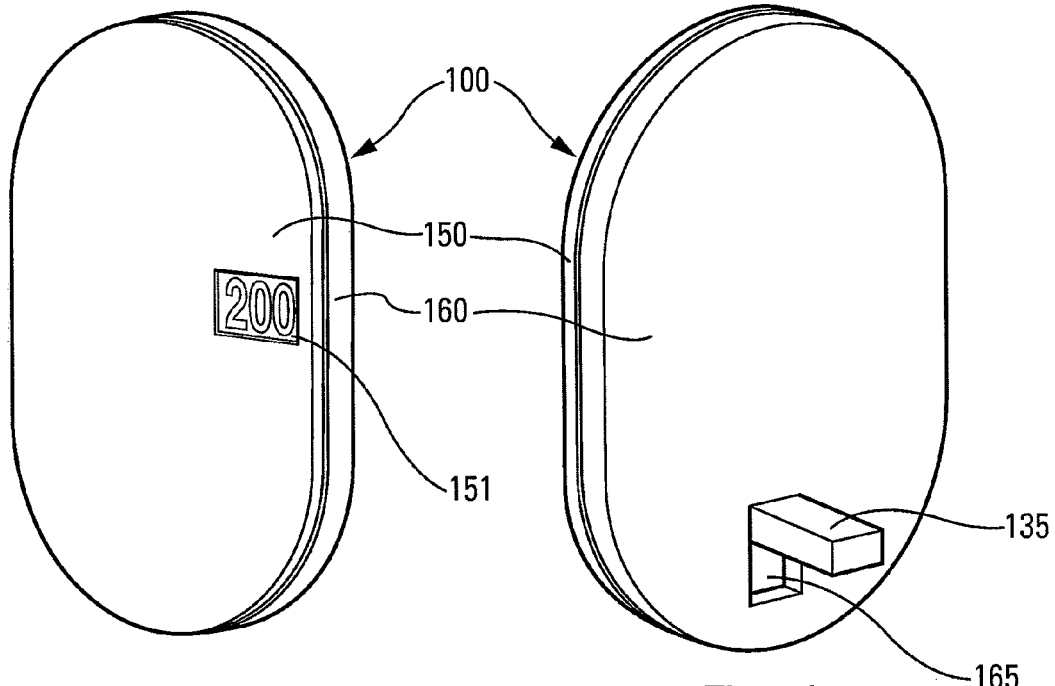
FIGS. 2a and 2b are two diagrammatic perspective views of the pre-assembled counter of FIG. 1, in front and rear views respectively.

FIG. 1 shows a dispenser device of the MDI 200 type, including, on its front main face, a dose counter 100 that corresponds to a particular embodiment of the present invention. The device includes a body 201 that is provided with a mouthpiece 202 that defines a dispenser orifice 203. A reservoir (not shown) is assembled in said body 201, said reservoir including a metering valve that is mounted on its opening. Inside said body 201, the metering valve co-operates with an expulsion channel that leads into the mouthpiece 202. When the user presses on the bottom of the reservoir, said reservoir slides axially inside the body 201, causing the valve to be actuated and a dose of fluid to be expelled. The operation of such an MDI-type device is well known to the person skilled in the art, and is therefore not described more fully below. The counter 100 may be interposed between the front main face of said body 201 and a covering member 250 that includes a window 251, and that may serve to fasten the counter 100 on the body. Naturally, this embodiment is only an example, and, by way of example, the counter could be fastened directly to the body 201, independently of the presence of a covering member. The counter includes an actuator element 135 that projects out from said counter, and that is adapted to penetrate inside the body 201 through an opening 210 that is provided for this purpose, so as to co-operate with the reservoir or with a portion that is secured to said reservoir. In this way, each time the dispenser device is actuated, the axial movement of the reservoir in the body 201 causes the actuator element 135 to move axially.

FIGS. 1 to 9 show a first embodiment with two rotary counter elements, and one intermediate element that is also rotary, and FIGS. 10 to 17 show a second embodiment with two rotary counter elements, but with no intermediate element.

In the first embodiment of the invention, the counter includes: two rotary counter elements, namely a first rotary counter element 110 and a second rotary counter element 120; an actuator member 130; and an intermediate rotary element 140. The actuator member 130 that includes the actuator element 135, is for transforming an axial movement of a portion of the dispenser device 200, generally the reservoir, into a turning movement of the first counter element 110.

In a preferred variant embodiment shown in FIG. 1, the counter is disposed on a face of the body 201 of the dispenser device 200, and the actuator member 130 thus transforms an axial movement of the reservoir into a turning movement of the first counter element 110. In this configuration, the three rotary elements 110, 120, 140 of the counter turn about pivot pins 161, 162 that are substantially perpendicular to the axial movement. Advantageously, the actuation cycle of the counter may start at the very beginning of the stroke of the reservoir, such that the counter is actuated before any fluid is dispensed.

The first rotary counter element 110 forms the units wheel, and the second rotary counter element 120 forms the tens wheel, said first and second counter elements co-operating with each other to define and to display, in a viewing window 151, the number of doses of fluid that have been dispensed or that remain to be dispensed from said reservoir. Preferably, this number is formed by a display zone in which the number is displayed horizontally when the dispenser device 200 is in its normal working position, shown in FIG. 1, in which the body 201 is substantially vertical with the mouthpiece 202 disposed at the bottom. Said first counter element 110 co-operates with the actuator member 130 that is adapted to cause said first counter element 110 to turn each time said actuator member is actuated. The intermediate rotary element 140 is adapted to cause said second counter element 120 to turn on every tenth actuation of said actuator member 130, and thus on every tenth turn of said first counter element 110. Said first and second counter elements 110, 120 turn about a common first pivot pin 161, and said intermediate element 140 turns about a second pivot pin 162 that is offset and parallel to said first pivot pin 161.

Figure 3:
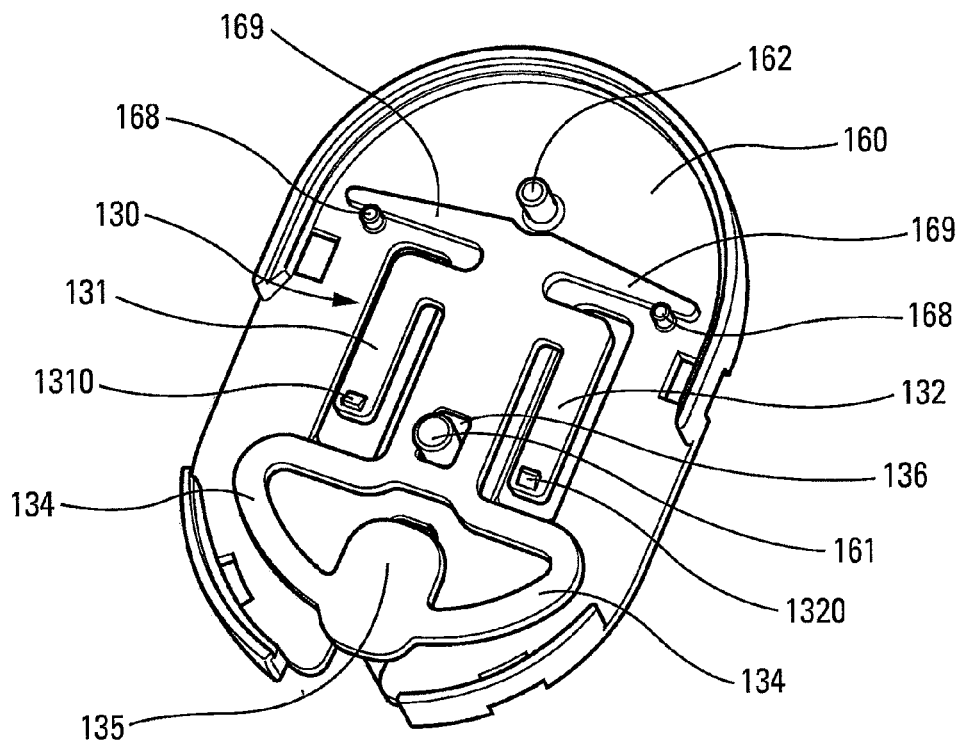
FIG. 3 is a diagrammatic perspective view of the actuator member in an advantageous embodiment of the invention.
Figure 4:
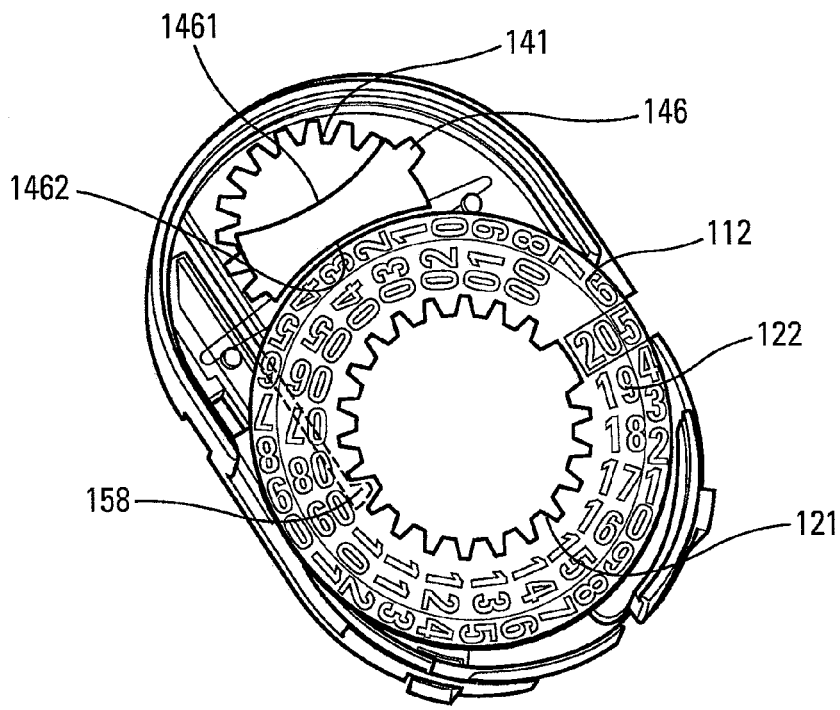
FIG. 4 is a partially-transparent diagrammatic perspective view of the two rotary counter elements and of the intermediate rotary element, in an advantageous embodiment of the invention, the intermediate element being in the assembled position.
Figure 5:
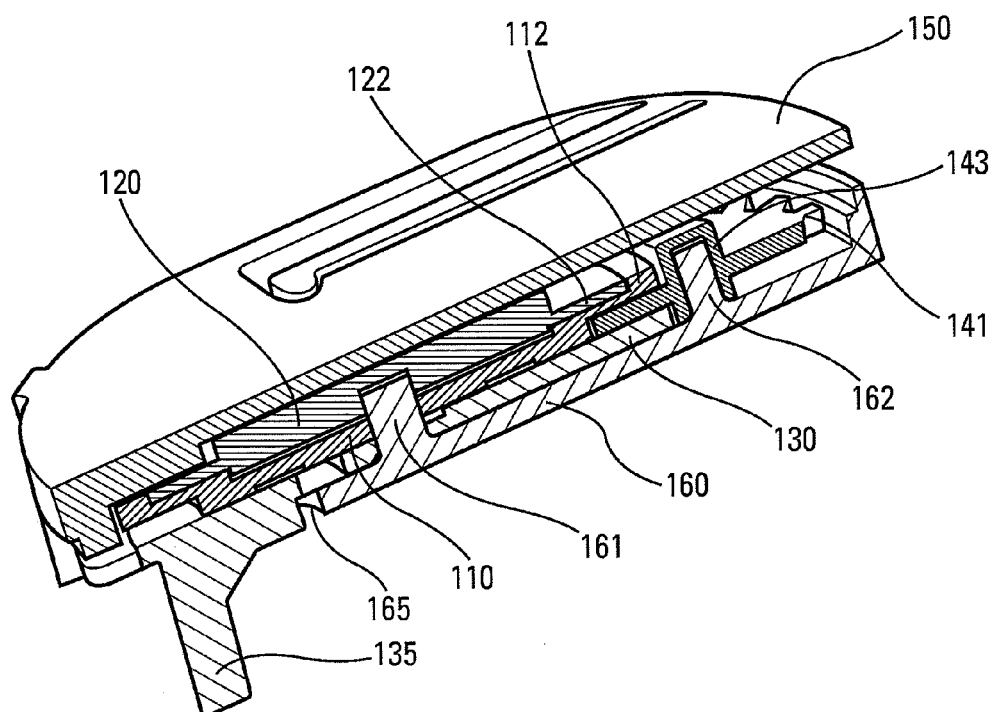
FIG. 5 is a diagrammatic section view in perspective of the counter, in an advantageous embodiment.
Figure 6:
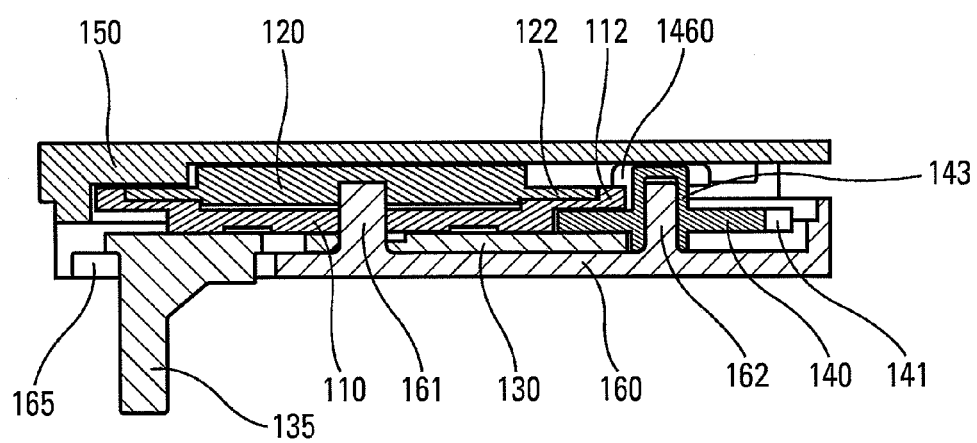
FIG. 6 is a diagrammatic cross-section view of the FIG. 5 counter.

As shown in FIGS. 3, 5, and 6, the counter preferably includes a base body 160 and a lid 150. Said base body forms the pivot pins 161 and 162, and includes an opening 165 through which the actuator element 135 is able to pass. The lid 150 includes a viewing window 151 enabling the user to see the display zone that is formed by said first and second counter elements together. Thus, said counter may advantageously be pre-assembled so as to form a counter unit, said counter unit possibly including fastener means for fastening to the body 201 of the fluid dispenser device 200. The fastener means are preferably formed on said base body.

Figure 7A:
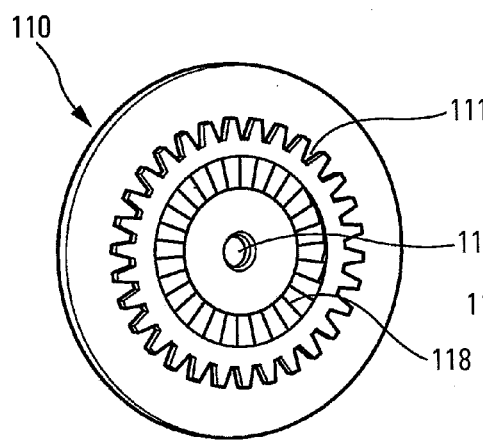
FIGS. 7a and 7b are diagrammatic rear and front views respectively of the first rotary counter element, in an advantageous variant embodiment.
Figure 7B:
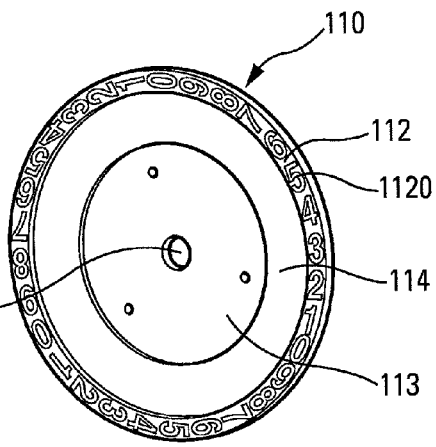

As shown in FIGS. 7a and 7b, said first counter element 110 may include a first peripheral set of teeth 118, which set, on each actuation, co-operates with at least one, preferably two flexible actuator tabs 131, 132 of the actuator member 130. A second peripheral set of teeth 111 is for co-operating, on each actuation, with the intermediate element 140. Advantageously, said first counter element 110 is substantially disk shaped, being provided with a central through opening 115 that is adapted to be engaged around its pivot pin 161. The top face of said disk includes a first radially-outer peripheral edge portion 112 that receives counter indices 1120, such as one or more series of numbers from 0 to 9. The example shown in FIG. 7b shows three series of numbers from 0 to 9, distributed over said periphery. The bottom face of said disk includes said first and second peripheral sets of teeth 118, 111, as visible in FIG. 7a. Preferably, the first set of teeth 118 is radially inside the second set of teeth 111, the teeth of the first set of teeth 118 being oriented axially, while the teeth of the second set of teeth are oriented radially outwards. The first set of teeth 118 and the two flexible tabs 131, 132 also form non-return means, preventing the first counter element 110 from turning in the opposite direction to the direction imparted thereto by the actuator member 130. As visible in FIGS. 7b, the top face of said first counter element 110 may include a central portion 113 that surrounds the central opening 115 and that is extended radially outwards by an intermediate portion 114 that is raised axially relative to said central portion 113. Said intermediate portion 114 is thus extended radially outwards by said first peripheral edge portion 112 that is raised axially relative to said intermediate portion. This embodiment makes it possible to superpose the second counter element 120 on the first counter element with an overall thickness that is small.

Figure 8A:
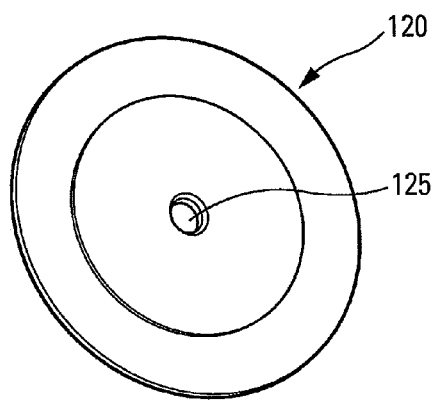
FIGS. 8a and 8b are diagrammatic rear and front views respectively of the second rotary counter element, in an advantageous variant embodiment.
Figure 8B:
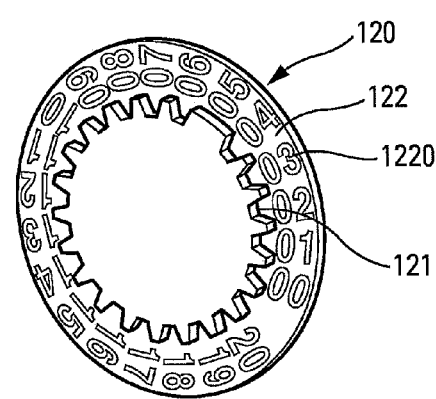

As shown in FIGS. 8a and 8b, said second counter element 120 may include a third peripheral set of teeth 121, which set is adapted, on every tenth actuation of the actuator member 130, to co-operate with said intermediate element 140. Advantageously, said second counter element is also substantially disk shaped, being provided with a central orifice 125 that, in the example shown, is blind, and that is adapted to be engaged around its pivot pin 161. The top face of said disk includes a second radially-outer peripheral edge portion 122 that receives counter indices 1220, such as the numbers from 00 to 20, distributed over said periphery. In this example, the counter is thus capable of counting 200 doses. The top face of said disk also includes said third peripheral set of teeth 121, disposed radially inside said second outer peripheral edge portion 122, said third peripheral set of teeth 121 being raised axially relative to said second outer peripheral edge portion 122. Advantageously, after assembling the first and second counter elements 110, 120 around their common pivot pin 161, said second outer peripheral edge portion 122 of said second counter element 120 is disposed radially inside, and substantially in contact with, said first outer peripheral edge portion 112 of said first counter element 110, the top surfaces of said first and second peripheral edge portions 112, 122 being substantially in alignment or coplanar, so as to form the display zone that is visible through the viewing window 151.

Figure 9A:
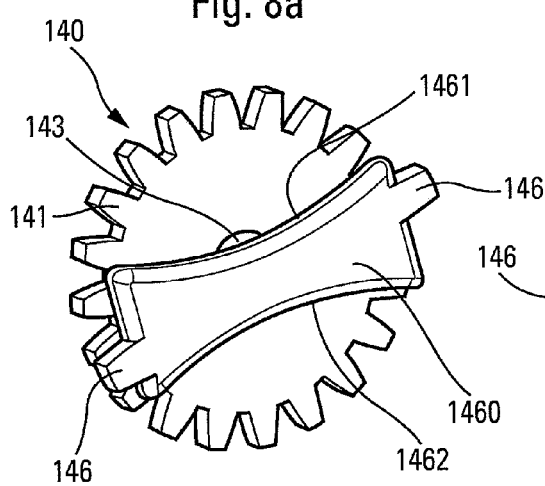
FIGS. 9a and 9b are diagrammatic front and rear views respectively of the intermediate rotary element, in an advantageous variant embodiment.
Figure 9B:
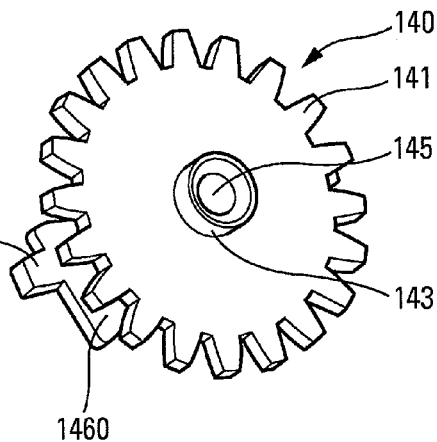

As visible in FIGS. 9a and 9b, said intermediate element 140 may include a fourth peripheral set of teeth 141, which set, on each actuation of the actuator member 130, co-operates with the second peripheral set of teeth 111 of said first counter element 110. In this way, each actuation of the dispenser device 200 is transformed, by the actuator member 130, into a turn of the first counter element 110. Advantageously, said intermediate element 140 also includes at least one radial projection 146 that, on every tenth actuation of the actuator member 130, co-operates with the third peripheral set of teeth 121 of the second counter element 120. The radial projection 146 may be formed on a radial rod portion 1460 of said intermediate element 140. Advantageously, said intermediate element 140 includes a central axial hollow sleeve 143, that, in the example shown, is blind, and that defines a central orifice 145 that is adapted to be engaged around its pivot pin 162. The fourth set of teeth 141 and said radial rod portion 1460 are offset relative to each other along said sleeve 143, defining between them a gap that may receive the first outer peripheral edge portion 112 of the first counter element 110, and the second outer peripheral edge portion 122 of the second counter element 120. Advantageously, said radial rod portion 1460 comprises two diametrally-opposite radially-outer projections 146 that are interconnected by a curved rod zone having side edges that are in the shape of circular arcs facing in substantially opposite directions, as clearly visible in FIGS. 4 and 9a. Thus, in an appropriate orientation, shown in FIG. 4, the first and second counter elements 110, 120 may be assembled one after the other on their common pivot pin 161, after the intermediate element 140 has been assembled on its own pivot pin 162. The present invention thus makes it possible to avoid two rotary elements of the counter needing to be assembled simultaneously around two offset pivot pins, as generally occurs with counters of this type.

Advantageously, said actuator member 130 is assembled in said base body 160. The lid 150 may include a flexible tab 158, visible in FIG. 4, that co-operates with the third set of teeth 121 of said second counter element 120, so as to prevent said second counter element 120 from turning in either direction when the intermediate element 140 is not co-operating with said second counter element 120. Naturally, said flexible tab 158 may deform resiliently so as to make it possible for said second counter element 120 to turn each time said intermediate element 140 co-operates with said second counter element 120, i.e. on every tenth actuation of said actuator member 130. Advantageously, abutment means are provided so as to form an abutment against axial movement of the flexible tabs 131, 132. The abutment means may advantageously be formed by the first projection 161 of the base body 160 that may co-operate with a window 136 of the actuator member 130. Other abutment means could also be envisaged. Each of the tabs 131 and 132 supports a respective lug 1310 and 1320 that co-operates with the first set of teeth 118 of the first counter element 110. The shapes of the lugs 1310 and 1320 are inverted such that the first lug 1310 pushes a tooth of the set of teeth 118 while the reservoir is descending in the body 201, and such that the second lug 1320 pulls a tooth while the reservoir is rising in the body 201. Advantageously, the flexible tabs 131 and 132 are substantially rigid axially and are flexible in a direction that is perpendicular to the axial movement of the actuator member 130. This enables the resilient tab, that does not act to turn the first counter element 110, to deform so as to slide over the set of teeth and engage in the next tooth. The two resilient tabs 131 and 132 also form the non-return means for the first counter element 110. Advantageously, the actuator member 130 includes resilient means 169, such as two resilient blades that co-operate with two appropriate shoulders 168 of the base body 160, so as to form a return spring for the actuator member 130. Preferably, the actuator member 130 further includes an axially deformable portion 134 that supports the actuator element 135. This makes it possible to continue the axial movement of the actuator element 135 (and thus of the reservoir) after the abutment position defined by the projection 161 and by the window 136 has been reached. The abutment may be formed such that a turn through exactly half a tooth is obtained while the reservoir is descending (when the first lug pushes the set of teeth 118), and such that the turn through the remaining half a tooth is obtained while the reservoir, and thus the actuator member 130, is rising under the effect of the resilient means 169 (when the second lug pulls on the set of teeth 118). Since the actuation of the valve generally requires a greater stroke, and thus a greater axial movement of the reservoir, the deformable portion 134 of the actuator member 130 makes it possible to continue the axial movement of the reservoir to its full stroke. In addition, the system makes it possible to actuate the counter before beginning to dispense the fluid.

In particular, the present invention makes it possible to simplify substantially the method of assembling a counter. Thus, the actuator member 130 is firstly assembled in said base body 160, with the actuator element 135 extending out from said base body 160 through said opening 165. Then, the intermediate rotary element 140 is assembled on its projection 162 of said base body. After appropriate orientation of said intermediate element in the assembled position shown in FIG. 4, the first rotary counter element 110 and then the second rotary counter element 120 may be assembled on their projection 161. Finally, the lid 150 may be assembled on said base body 160, so as to form a pre-assembled counter unit.

The counter of the invention also presents the advantage of being very thin, thereby enabling the outside dimensions of the device to be reduced, and the handling of the device to remain substantially unmodified. In particular, the pre-assembled counter unit comprising the base body 160, the actuator member 130, the intermediate element 140, the first and second counter elements 110, 120, and the lid 150 may have thickness that is less than or equal to 7 mm, advantageously less than 6 mm, in particular less than 5 mm. Naturally, these measurements do not take account of the actuator element 135 that projects out from the pre-assembled counter unit in the thickness direction.

In advantageous manner, the counter is actuated in two stages, a first stage prior to dispensing the fluid through the dispenser orifice 203 of the body 201, and a second stage after the fluid has been dispensed. Advantageously, the counter does not operate while the fluid is actually being dispensed, and its safe and reliable operation is thus completely independent of the way in which the user actuates the device in order to dispense fluid.

Naturally, compared with the above description, the counter could be made in a manner that is different from the manner shown. In particular, the shapes and positions of the first and second flexible tabs 131 and 132 could be different. It could also be envisaged to invert the functions of the first and second flexible tabs 131, 132, i.e. the first flexible tab 131 could pull the first counter element 110, while the second flexible tab 132 could push it. In addition, the shape of the deformable portion 134 that supports the actuator element 135 could be different from the shape shown in FIG. 3.

In the second embodiment of the invention, the counter likewise includes two rotary counter elements, namely a first rotary counter element 410, shown in detail in FIGS. 17*a* and 17*b*, and a second rotary counter element 420, shown in detail in FIGS. 16*a* and 16*b*, and an actuator member 430. The actuator member 430 that includes the actuator element 435, is for transforming an axial movement of a portion of the dispenser device, generally the reservoir, into a turning movement of the first counter element 410. However, in this embodiment there is no intermediate rotary element for interconnecting the first and second counter elements, but it is the first counter element that includes means that are adapted to co-operate with the second counter element.

In a preferred variant embodiment the counter is disposed on a face of the body of the dispenser device, and the actuator member 430 thus transforms an axial movement of the reservoir into a turning movement of the first counter element 410. In this configuration, the two rotary elements 410, 420, of the counter turn about a pivot pin 461 that is substantially perpendicular to the axial movement. Advantageously, the actuation cycle of the counter may start at the very beginning of the stroke of the reservoir, such that the counter is actuated before any fluid is dispensed.

The first rotary counter element 410 forms the units wheel, and the second rotary counter element 420 forms the tens wheel, said first and second counter elements co-operating with each other to define and to display, in a viewing window (not shown), the number of doses of fluid that have been dispensed or that remain to be dispensed from said reservoir. Preferably, this number is formed by a display zone in which the number is displayed horizontally when the dispenser device is in its normal working position in which the body is substantially vertical with the mouthpiece disposed at the bottom. Said first counter element 410 co-operates with the actuator member 430 that is adapted to cause said first counter element 410 to turn each time said actuator member is actuated. Interconnection means are adapted to cause said second counter element 420 to turn on every tenth actuation of said actuator member 430, and thus on every tenth turn of said first counter element 410. Both counter elements are advantageously assembled in rotary manner around the same pivot pin 461.

As shown in FIGS. 10 to 15, the counter preferably includes a base body 460 to which a lid (not shown) may be associated. Said base body forms the pivot pin 461, and includes an opening 465 through which the actuator element 435 is able to pass. The lid may include a viewing window enabling the user to see the display zone that is formed by said first and second counter elements 410, 420 together. The base body 460 may include fastener means 467, such as snap-fastener tabs, that are adapted to fasten the outer edge of the second counter element 420, without however limiting its capacity to turn about its pin 461. The second counter element 420 retains the first counter element 410 that in turn retains the actuator member 430 in the base body 460. Thus, said counter may advantageously be pre-assembled so as to form a counter unit, said counter unit possibly including fastener means for fastening to the body of the fluid dispenser device. Preferably, the fastener means are formed on said base body.

Figure 10:
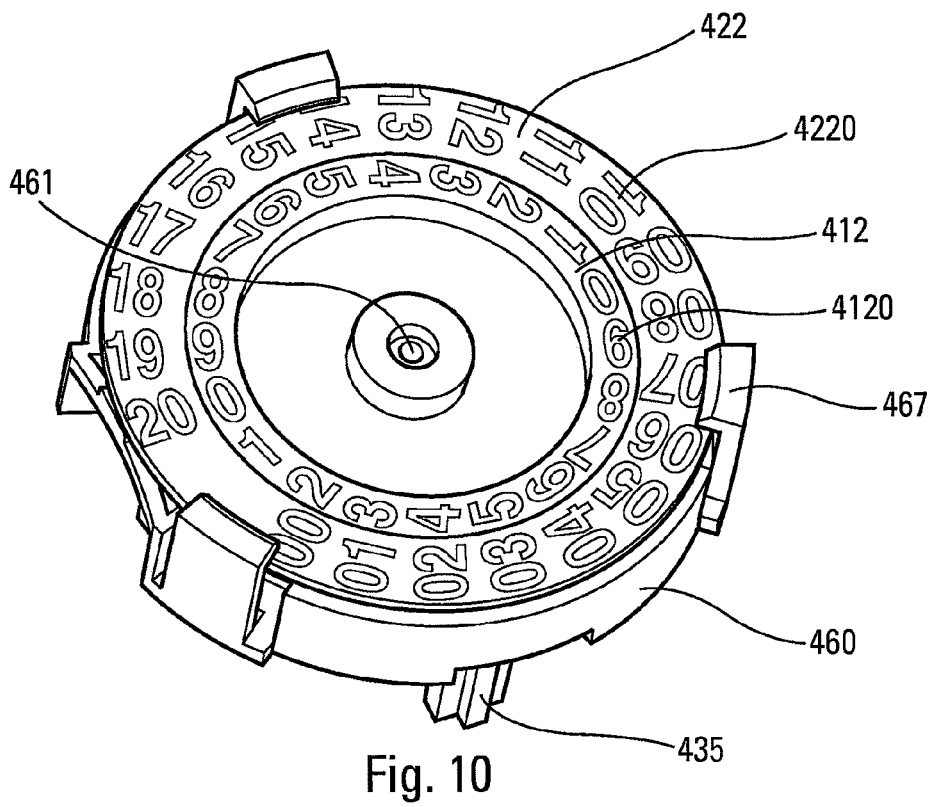
FIG. 10 is a diagrammatic perspective view from in front of a counter, in an advantageous embodiment of the present invention.
Figure 11:
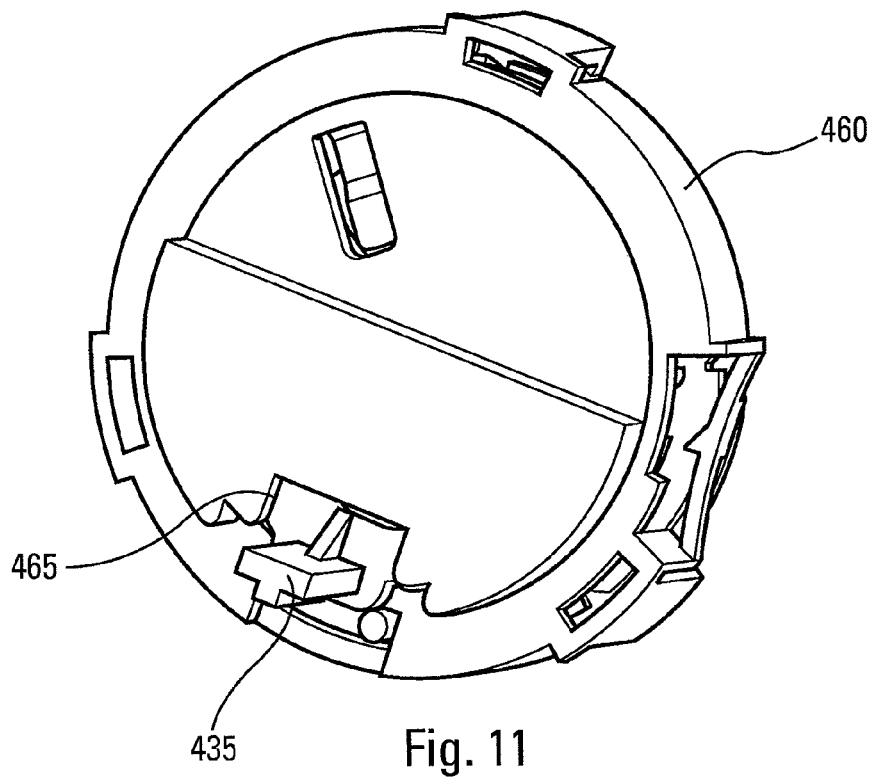
FIG. 11 is a view similar to the view in FIG. 10, but as seen from behind.
Figure 12:
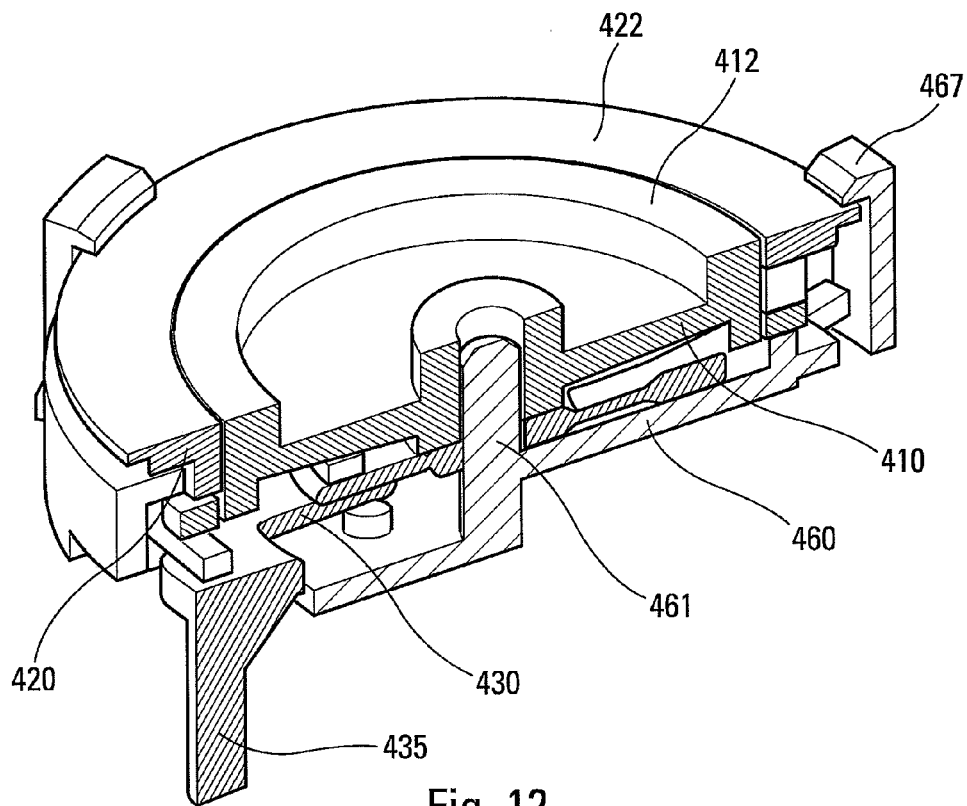
FIG. 12 is a diagrammatic perspective view partially in section of the two rotary counter elements and of the intermediate rotary element, in an advantageous embodiment of the invention, the intermediate element being in the assembled position.
Figure 13:
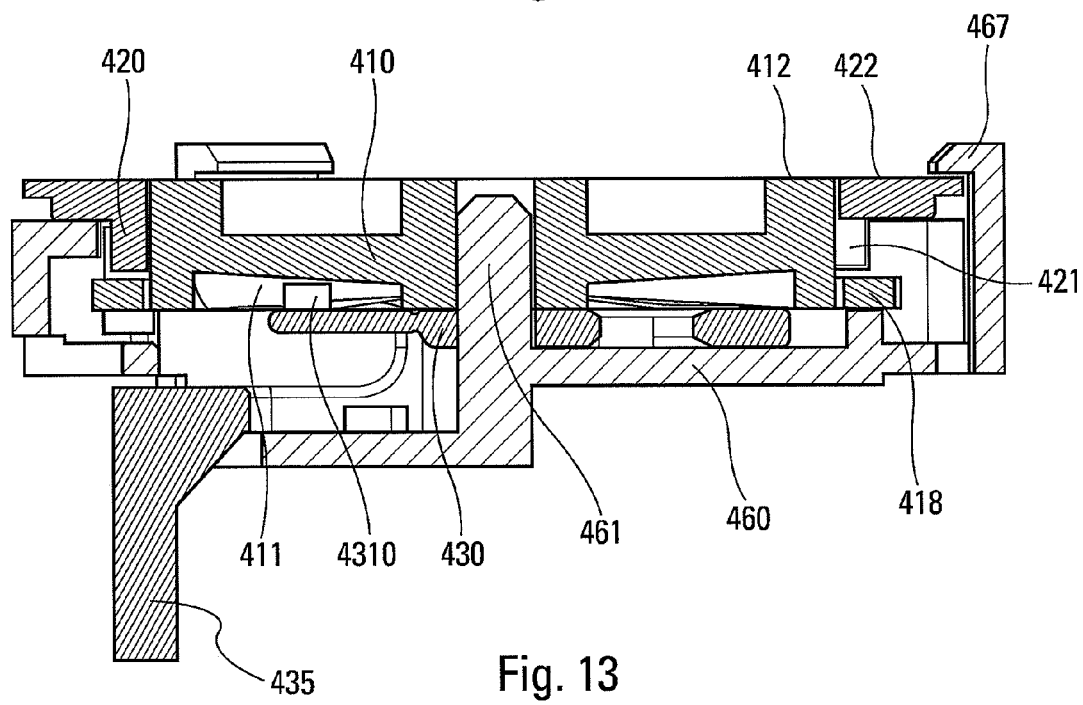
FIG. 13 is a diagrammatic cross-section view of the FIG. 12 counter.

As shown in FIGS. 17*a* and 17*b*, said first counter element 410 may include a first peripheral set of teeth 411, which set, on each actuation, co-operates with a flexible actuator tab 431 of the actuator member 430. Advantageously, said first counter element 410 is substantially disk shaped, being provided with a central through opening 415 that is adapted to be engaged around its pivot pin 461. The top face of said disk includes a first peripheral edge portion 412 that receives counter indices 4120, such as one or more series of numbers from 0 to 9. The example shown in FIG. 10 shows two series of numbers from 0 to 9, distributed over said periphery. The bottom face of said disk includes said first peripheral set of teeth 411, as can be seen in FIG. 17*b*. Preferably, the teeth of the first set of teeth 411 are oriented axially. As visible in FIG. 17*a*, the top face of said first counter element 410 may include a central plane portion that surrounds the central opening 415 and that is extended radially outwards by said first peripheral edge portion 412 that is raised axially relative to said central portion. The peripheral edge portion 412 is extended radially outwards by an outer plane portion 413 that does not extend over the entire periphery, but that is interrupted by at least one, preferably two, flexible tabs 418 each of which includes a respective lug 419 at its end. The flexible tabs 418 preferably extend in peripheral manner, and the lug 419 may extend perpendicularly to its respective tab 418, as visible in FIGS. 17a and 17b. This embodiment makes it possible to superpose the second counter element 420 on the first counter element 410 with an overall thickness that is small.

As shown in FIGS. 16a and 16b, said second counter element 420 may include a second peripheral set of teeth 421, which set is adapted, on every tenth actuation of the actuator member 430, to co-operate with a lug 419 of said first counter element 410. Advantageously, said second counter element is substantially ring shaped, adapted to be disposed on said outer portion 413 of said first counter element 410. The top face of said ring includes a second radially-outer peripheral edge portion 422 that receives counter indices 4220, such as the numbers from 00 to 20, distributed over said periphery. In this example, the counter is thus capable of counting 200 doses. The bottom face of said ring includes said second peripheral set of teeth 421, disposed radially inside, and extending axially downwards, and a third peripheral set of teeth 426, disposed radially outside said bottom face. The third set of teeth 426 is adapted to co-operate with at least one projection that is provided on the base body 460 so as to act as non-return means. Advantageously, after assembling the first and second counter elements 410, 420 around their common pivot pin 461, said second peripheral edge portion 422 of said second counter element 420 is disposed radially outside, and substantially in contact with, said first peripheral edge portion 412 of said first counter element 410, the top surfaces of said first and second peripheral edge portions 412, 422 being substantially in alignment or coplanar, so as to form the display zone that is visible through the viewing window.

The first counter element 410 includes at least one deformable finger 418, preferably two diametrally-opposite fingers, the deformable finger(s) being adapted, on every tenth actuation, to co-operate with a cam that is secured to the base body. A plurality of cams may optionally be provided. The second set of teeth 421 of the second counter element 420 is for co-operating with the lug 419 of a deformable finger 418 of the first counter element each time said deformable finger is moved towards its deformed position by said cam. More clearly, the cam provided in said base body is adapted to deform a deformable finger 418 resiliently and radially inwards, each time the lug 419 of said deformable finger 418 co-operates with said cam. When the finger 418 is not deformed, said lug 419 does not co-operate with said second set of teeth 421.

In the example shown in the drawings, the first counter element 410 includes two diametrally-opposite fingers 418, and two series of numbers from 0 to 9, distributed over the periphery. On every tenth actuation, one of the two deformable fingers 418 co-operates with said cam, preferably provided radially on the outside relative to said fingers, so as to deform them inwards and enable said lug 419 to co-operate with the second set of teeth 421 of the second counter element 420. The second counter element 420 is thus also turned. The third set of teeth 426 of the second counter element 420 is for co-operating with non-return means, e.g. a projection that may be secured to the base body 460. It should be noted that the non-return means could equally well co-operate with the second set of teeth, in which situation the second counter element 420 could include a single set of teeth only.

An advantage of the counter of the present invention is that it makes a large display possible, without increasing the bulkiness of the counter. In particular, the embodiment shown makes it possible for a 200-dose counter to display numbers (firstly units, secondly tens) having a height that is greater than 2 mm, preferably about 2.5 mm, and a width that is greater than 1.5 mm, preferably about 2 mm. This represents an increase in the physical size of the numbers of up to 50% relative to existing counters.

In the embodiment shown, the indicator is adapted to indicate the number of doses that remain to be dispensed, such that the number displayed decreases on each actuation. Naturally, the inverse is also possible, namely a counter that counts the number of doses that have been dispensed.

Figure 14:
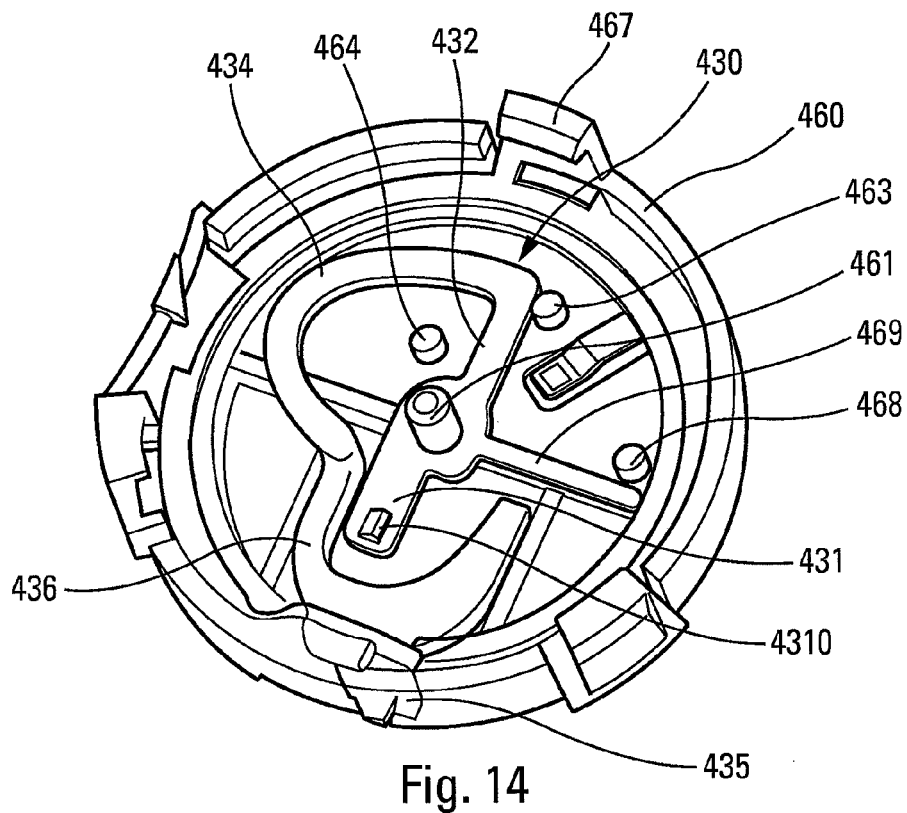
FIG. 14 is a partially-transparent diagrammatic perspective view from in front of the actuator member of the counter, in an advantageous embodiment, shown assembled in the base body.
Figure 15:
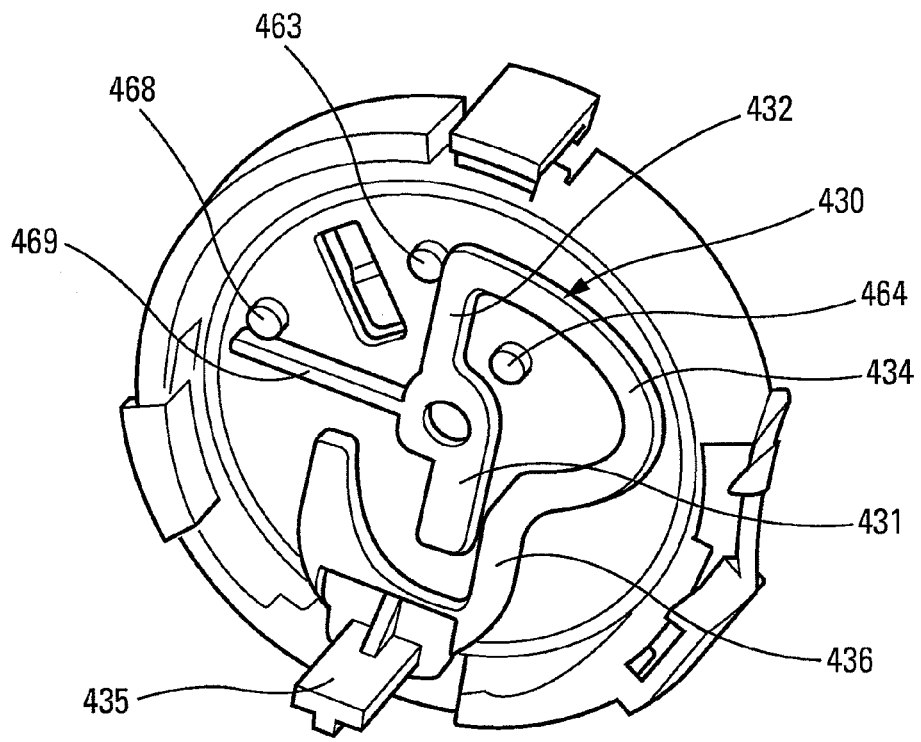
FIG. 15 is a view similar to the view in FIG. 14, but as seen from behind.

Advantageously, said actuator member 430 is assembled in said base body 460 by being engaged around the pivot pin 461, in particular as visible in FIGS. 14 and 15. The actuator member includes a tab 431 that supports a lug 4310 that is adapted to co-operate with the first set of teeth 411 of the first counter element 410. The tab 431 may extend downwards from the pivot pin 461, when the counter is in its normal vertical working position. However, it could equally well extend in another direction, e.g. horizontally in the working position. The tab 431 is extended on another side of the pivot pin 461 by a substantially rigid rectilinear portion 432, itself connected to an elastically-deformable portion 434 forming a loop making it possible to pass around the pivot pin 461. The elastically-deformable portion 434 is extended axially by a rigid support portion 436 that supports the actuator element 435 that is movable axially. Advantageously, abutment means 463, 464 are provided so as to form an abutment to the turning movement of the tab 431. The abutment means may advantageously be formed by two projections 463, 464 from the base body 460 that may co-operate with the substantially rigid rectilinear portion 432 that extends the tab 431 on the other side of the pivot pin 461 in the embodiment shown in the figures. Other abutment means could also be envisaged. Thus, on each actuation, the actuator element 435 is moved axially downwards, causing the tab 431 to turn around the pivot pin 461. When the abutment position of the tab 431 is reached, the actuator element 435 can continue its axial movement by means of the elastically-deformable portion 434. Advantageously, the tab 431 is substantially rigid axially and is flexible in a direction that is perpendicular to the plane of the base body 460. This enables the tab 431 to deform a little so as to enable the lug 4310 to slide over the set of teeth 411 and engage in the next tooth. Advantageously, the actuator member 430 includes resilient means 469, such as a resilient blade that co-operates with an appropriate shoulder 468 of the base body 460, so as to form a return spring for the actuator member 430. In the embodiment shown, the resilient blade 469 extends perpendicularly to the flexible tab 431. Naturally, if the flexible tab 431 extended in another direction (e.g. the direction of the resilient blade 469 in FIG. 14), then the resilient blade would also extend in another direction. In particular, the resilient blade 469 and the flexible tab 431 could be inverted relative to the FIGS. 14 and 15. The axially deformable portion 434 of the actuator member 430 that supports the actuator element 435 makes it possible to continue the axial movement of the actuator element 435 (and thus of the reservoir) after the abutment position of the tab 431 defined by the projection has been reached. The abutment may be formed such that a turn of exactly one tooth is obtained when the abutment position is reached. Since the actuation of the valve generally requires a greater stroke, and thus a greater axial movement of the reservoir, the deformable portion 434 of the actuator member 430 makes it possible to continue the axial movement of the reservoir to its full stroke.

In addition, the system makes it possible to actuate the counter before beginning to dispense the fluid.

As a result of its components and the arrangement thereof, the counter of the second embodiment may also be made to be thin. In particular, the pre-assembled counter unit comprising the base body 460, the actuator member 430, and the first and second counter elements 410, 420 may have thickness that is less than or equal to 7 mm, advantageously less than 6 mm, in particular less than 5 mm. Naturally, these measurements do not take account of the actuator element 435 that projects out from the pre-assembled counter unit in the thickness direction.

Various modifications may also be envisaged by a person skilled in the art, without going beyond the ambit of the present invention, as defined by the accompanying claims.

The invention claimed is:

1. A dose counter for counting the number of doses of fluid or powder that have been dispensed or that remain to be dispensed from a fluid dispenser device, said counter including a first rotary counter element forming a units wheel, and a second rotary counter element forming a tens wheel, said first and second counter elements co-operating with each other to define and to display, in a viewing window, said number of doses, said first counter element co-operating with an actuator member that is adapted to cause said first counter element to turn each time said actuator member is actuated, said counter including a base body that incorporates a pivot pin for said first and second counter elements, said body including fastener means and receiving said actuator member and said first and second counter elements, such that said first counter element retains said actuator member in said base body and said second counter element retains said first counter element in said base body, said fastener means retaining said second counter element in said base body, such that said counter is pre-assembled in said base body so as to form a pre-assembled counter unit separate from the fluid dispenser device before the counter unit is assembled to the fluid dispenser device; and wherein the fastener means is formed on the base body and forms a one-piece construction with the base body.

2. A counter according to claim 1, wherein said counter unit includes body fastener means for fastening to a body of a fluid dispenser device.

3. A counter according to claim 2, wherein said body fastener means are formed on said base body.

4. A counter according to claim 1, wherein said base body is associated with a lid that is adapted to be fastened on said base body, after the counter has been pre-assembled in said base body.

5. A counter according to claim 4, wherein the pre-assembled counter unit, comprising the base body, the actuator member, an intermediate element, the first and second counter elements, and the lid, presents a thickness that is less than or equal to 7 mm.

6. A counter according to claim 1, wherein the pre-assembled counter unit, comprising the base body, the actuator member, and the first and second counter elements, presents a thickness that is less than or equal to 7 mm.

7. A fluid or powder dispenser device comprising a reservoir, a dispenser member that is mounted on said reservoir, and a body incorporating a dispenser orifice, said reservoir being movable in said body so as to dispense the fluid or powder, said dispenser device comprising a counter according to claim 1.

8. A device according to claim 7, wherein said counter is fastened to the body laterally, said device being actuated by the user pressing axially on the reservoir, and said counter being actuated by said axial movement of said reservoir that co-operates with said actuator element of the actuator member.

9. The counter according to claim 1, wherein said fastener means are snap-fastener tabs that cooperate with an outer edge of said second counter element without limiting a capacity of said second counter element.

10. A dose counter for counting a number of doses of fluid or powder that have been dispensed or that remain to be dispensed from a fluid dispenser device, comprising:

a first rotary counter element forming a units wheel;

a second rotary counter element forming a tens wheel, the first counter element and the second counter element co-operating with each other to indicate the number of doses;

an actuator member cooperating with the first counter element to cause the first counter element to turn each time the actuator member is actuated; and a base body comprising a pivot pin on which the first counter element and the second counter element are rotationally supported;

the base body containing the actuator member, the first counter element and the second counter element, such that the first counter element retains the actuator member in the base body and the second counter element retains the first counter element in the base body; and the base body comprising a fastener that retains the second counter element in the base body, together forming a pre-assembled counter unit comprising the base body, the actuator member, the first counter element and the second counter element; and wherein the fastener is formed on the base body and forms a one-piece construction with the base body.

11. A fluid dispenser device comprising a housing, the dose counter of claim 10 within the housing, and a window through which the number of doses is viewable.

12. The counter according to claim 10, wherein the base body is associated with a lid adapted to be fastened on the base body, after the counter has been pre-assembled in the base body.

13. The counter according to claim 12, wherein the pre-assembled counter unit presents thickness that is less than or equal to 7 mm.

14. A fluid or powder dispenser device comprising a reservoir, a dispenser member mounted on the reservoir, and a body incorporating a dispenser orifice, the reservoir movable in the body so as to dispense the fluid or powder, the device further comprising the counter according to claim 10.

15. The device according to claim 14, wherein the counter is fastened to the body laterally, the device actuated by pressing axially on the reservoir, and the counter actuated by axial movement of the reservoir that co-operates with the actuator element of the actuator member.

16. A dose counter for counting a number of doses of fluid or powder that have been dispensed or that remain to be dispensed from a fluid dispenser device, comprising:

a first rotary counter element forming a units wheel;

a second rotary counter element forming a tens wheel, the first counter element and the second counter element co-operating with each other to indicate the number of doses;

an actuator member cooperating with the first counter element to cause the first counter element to turn each time the actuator member is actuated; and a base body comprising a pivot pin on which the first counter element and the second counter element are rotationally supported;

the base body containing the actuator member, the first counter element and the second counter element, such that the first counter element retains the actuator member in the base body and the second counter element retains the first counter element in the base body; and the base body comprising a fastener that retains the second counter element in the base body, together forming a pre-assembled counter unit comprising the base body, the actuator member, the first counter element and the second counter element; and wherein the fastener comprises snap-fastener tabs that cooperate with an outer edge of the second counter element.

17. The counter according to claim 4, wherein the pre-assembled counter unit, comprising the base body, the actuator member, an intermediate element, the first and second counter elements, and the lid, presents thickness that is less than or equal to 6 mm.

18. The counter according to claim 4, wherein the pre-assembled counter unit, comprising the base body, the actuator member, an intermediate element, the first and second counter elements, and the lid, presents thickness that is less than or equal to 5 mm.

19. The counter according to claim 1, wherein the pre-assembled counter unit, comprising the base body, the actuator member, and the first and second counter elements, presents thickness that is less than or equal to 6 mm.

20. The counter according to claim 1, wherein the pre-assembled counter unit, comprising the base body, the actuator member, and the first and second counter elements, presents thickness that is less than or equal to 5 mm.

\* \* \* \* \*